(12) United States Patent
Schreiber et al.

(10) Patent No.: US 7,333,894 B2
(45) Date of Patent: Feb. 19, 2008

(54) METHODS FOR THE DIAGNOSIS OF HEMODIALYSIS PATIENTS AND UTILIZATION OF SUCH METHODS TO IMPROVE THE ADMINISTRATION OF INTRAVENOUS LEVOCARNITINE TREATMENTS TO HEMODIALYSIS PATIENTS

(75) Inventors: Brian Schreiber, Neenah, WI (US); Vyonne T. Lewis, New Orleans, LA (US)

(73) Assignee: Sigma-Tau Pharmaceuticals, Inc., Gaithersburg, MD (US)

(*) Notice: Subject to any disclaimer, the term of this patent is extended or adjusted under 35 U.S.C. 154(b) by 665 days.

(21) Appl. No.: 10/355,263

(22) Filed: Jan. 31, 2003

(65) Prior Publication Data

US 2003/0225162 A1 Dec. 4, 2003

Related U.S. Application Data

(60) Provisional application No. 60/352,505, filed on Jan. 31, 2002.

(51) Int. Cl.
*G01N 33/48* (2006.01)
(52) U.S. Cl. ............................. 702/19; 702/20; 703/11; 707/102
(58) Field of Classification Search .................. 702/19, 702/20; 703/11; 707/102
See application file for complete search history.

(56) References Cited

U.S. PATENT DOCUMENTS

| | | | | |
|---|---|---|---|---|
| 5,255,187 | A | * | 10/1993 | Sorensen ..................... 600/300 |
| 5,747,274 | A | * | 5/1998 | Jackowski ................. 435/7.94 |
| 6,149,585 | A | * | 11/2000 | Gray .......................... 600/300 |
| 7,011,977 | B2 | * | 3/2006 | Chace et al. .................. 436/86 |
| 2003/0083901 | A1 | * | 5/2003 | Bosch et al. ..................... 705/2 |
| 2003/0178031 | A1 | * | 9/2003 | Du Pen et al. ............. 128/898 |
| 2004/0111293 | A1 | * | 6/2004 | Firanek et al. .................. 705/2 |
| 2004/0111294 | A1 | * | 6/2004 | McNally et al. ................ 705/2 |
| 2004/0122703 | A1 | * | 6/2004 | Walker et al. .................. 705/2 |
| 2004/0122787 | A1 | * | 6/2004 | Avinash et al. ............... 706/50 |

OTHER PUBLICATIONS

LoVecchio, F. et al. 1997 Emergency Medicine Clinics of north America, vol. 15, No. 3 pp. 605-623.*
Sakurabayashi, T. et al. American Journal of Nephrology (1999) vol. 19, pp. 480-484.*
Printout from Trademark Electronic Search System for mark of FLORINEF, printed Oct. 18, 2006.*
Nyhan, William L., M/D.; Abnormalities of Fatty Acid Oxidation; 1988; 319:1344-1346.
FDA Report, F-D-C Repots; "The Pink Sheet"; Oct. 30, 1989; vol. 51, Issue 44.
Evans, Allan M.; Faull, Randall; Fornasini, Gianfranco; Lemanowicz, Edward; Longo, Antonio; Pace Silvia; Nation, Roger; Pharmacokinetics of L-Carnitine in Patients with End-Stage Renal Disease Undergoing Long-Term Hemodialysis; 2000; 68(3)238-249.
Wanner, Christoph; Hörl; Carnitine Abnormalities in Patients with Renal Insufficiency: Pathophysiological and Therapeutical Aspects; 1888; 50:89-102.
Riley, S.; Rutherford, S.; Rutherford, P.A.; Low Carnitine Levels in Hemodialysis Patients: Relationship with Functional Activity Status and Intra-Dialytic Hypotension; 1997; 48:6-7.
Rebouche, Charles; Engel, Andrew; Primary Systemic Carnitine Deficiency: I. Carnitine Biosynthesis 1989; 31:813-818.
Brass, Eric; Pharmacokinetic Considerations for the Therapeutic Use of Carnitine in Hemodialysis Patients; 1995; 17(2):176-185.
Van Es. A; Henny, F.C.; Koolstra, M.P.; Lobatto, S.; Scholte, H.R.; Amelioration of Cardiac Function by L-Carnitine Administration in Patients on Haemodialysis; 1992; 98:28-35.
Spagnoli, Luigi G.; et al.; Morphometric Evidence of the Trophic Effect of L-Carnitine on Human Skeletal Muscle; 1990: 55:16-23.
Vacha, Gian Maria, et al.; L-Carnitine Addition to Dialysis Fluid: A Therapeutic Alternative for Hemodialysis Patients; 1989; 51:237-242.
Siami, Ghodrat, et al.; Evaluation of the Effect of Intravenous L-Carnitine Therapy on Function, Structure and Fatty Acid Metabolism of Skeletal Muscle in Patients Receiving Chronic Hemodialysis; 1991; 57:306-313.
Ahmad, Suhail, et al.; Multicenter Trial of L-Carnitine in Maintenance Hemodialysis Patients. II. Clinical and Biochemical Effects; 1990; 38:912-918.
Ahmad, S., et al.; Role of L-Carnitine in Treating Renal Dialysis Patients; 1994; 23:177-181.

* cited by examiner

*Primary Examiner*—Mary K. Zeman
(74) *Attorney, Agent, or Firm*—Hogan & Hartson

(57) ABSTRACT

The disclosed invention pertains to methods for diagnosing clinical conditions that are common in hemodialysis patients and that may be related to abnormal carnitine metabolism resulting from hemodialysis. Further, the present invention pertains to methods for monitoring and improving the administration of therapeutic intravenous levocarnitine to such patients. Clinical algorithms have been developed for the clinical symptoms seen in end-stage renal disease (ESRD) patients that may be related to carnitine deficiency. Monitoring tools to assist healthcare professionals in implementing the clinical algorithms are also provided.

19 Claims, 18 Drawing Sheets

CARDIOMYOPATHY                                              CHARTING TOOL

PATIENT NAME _____ I.D. # _____

TREATMENT CONSIDERATIONS

|  | YES | NO | NRT* |
|---|---|---|---|
| • CONTROL VOLUME | ☐ | ☐ | ☐ |
| • TREAT ARRYTHMIA | ☐ | ☐ | ☐ |
| • TREATE ARRYTHMIA | ☐ | ☐ | ☐ |
| • ADJUST HCT/HGB | ☐ | ☐ | ☐ |
| • REDUCE AFTER-LOAD | ☐ | ☐ | ☐ |
| • EVALUATE PRE-DIALYSIS PLASMA CARNITINE LEVEL | ☐ | ☐ | |
| • BELOW NORMAL PRE-DIALYSIS PLASMA CARNITINE LEVEL (<40–50 μmol/L) | ☐ | ☐ | |

RE-EVALUATE BY CLINICAL EXAM TO BE CERTAIN THAT THERAPIES GIVEN ARE ADEQUATE.

SIGNATURE _____ DATE _____   *NRT= NO RESPONSE TO THERAPY

FIG.3

*CARDIAC ARRHYTHMIAS* _____ *CHARTING TOOL*

PATIENT NAME _____ I.D. # _____

UNDERLYING MEDICAL CONDITION:

|  | YES | NO | NRT* |
|---|---|---|---|
| • ISCHEMIC HEART DISEASE | ☐ | ☐ | ☐ |
| • THYROID DISEASE | ☐ | ☐ | ☐ |
| • ELECTROLYTE ABNORMAL | ☐ | ☐ | ☐ |
| • CHRONIC LUNG DISEASE | ☐ | ☐ | ☐ |
| • DRUGS (DIGOXIN, THEOPHYLLINE, ANTIARRHYTHMICS, ETC.) | ☐ | ☐ | ☐ |

DIALYSIS RELATED EFFECT:

|  | YES | NO | NRT* |
|---|---|---|---|
| • OPTIMIZE VOLUME STATUS | ☐ | ☐ | ☐ |
| • ADJUST DIALYSATE (K+) | ☐ | ☐ | ☐ |
| • INADEQUATE DIALYSIS | ☐ | ☐ | ☐ |
| • OXYGEN ON DIALYSIS | ☐ | ☐ | ☐ |
| • EVALUATE PRE-DIALYSIS PLASMA CARNITINE LEVEL | ☐ | ☐ | ☐ |
| • BELOW NORMAL PRE-DIALYSIS PLASMA CARNITINE LEVEL (<40-50 µmol/L) | ☐ | ☐ | ☐ |

*RE-EVALUATE BY CLINICAL EXAM TO BE CERTAIN THAT THERAPIES GIVEN ARE ADEQUATE.*

SIGNATURE _____ DATE _____ *NRT= NO RESPONSE TO THERAPY

FIG.5

MUSCLE WEAKNESS                                                     CHARTING TOOL

PATIENT NAME _____ I.D. # _____

YES    NO    NRT*
- WEAKNESS IN ARTHRITIC OR INJURED JOINT                 □      □      □
- SENSORY ABNORMALITY PRESENT                            □      □      □
- STRETCH REFLEXES                                       □      □      □
- IS MUSCLE WEAKNESS RELATING TO MYOPATHY?               □      □      □

IF YES, THEN PROCEED TO DIAGNOSIS TOOL ON MYOPATHY.
IF NO, THEN PROCEED TO DIAGNOSIS TOOL ON MALAISE/FATIGUE.

RE-EVALUATE BY CLINICAL EXAM TO BE CERTAIN THAT THERAPIES GIVEN ARE ADEQUATE.

SIGNATURE _____ DATE _____  *NRT= NO RESPONSE TO THERAPY

FIG.7

MUSCLE MYOPATHY                                                        CHARTING TOOL

PATIENT NAME _____ I.D. # _____

AFTER RULING OUT MUSCLE WEAKNESS AS OUTLINED IN THE ALGORITHM, PROCEED AS FOLLOWS:

|  | YES | NO | NRT* |
|---|---|---|---|
| • INFECTIOUS/INFLAMATORY/MALIGNANT | ☐ | ☐ | ☐ |
| • THYROID DISORDER | ☐ | ☐ | ☐ |
| • CUSHING'S DISEASE | ☐ | ☐ | ☐ |
| • ALCOHOL/DRUGS | ☐ | ☐ | ☐ |
| • UNCONTROLLED HYPERPARATHYROIDISM | ☐ | ☐ | ☐ |
| • OSTEOMALACIA | ☐ | ☐ | ☐ |
| • ALUMINUM TOXICITY | ☐ | ☐ | ☐ |
| • EVALUATE PRE-DIALYSIS PLASMA CARNITINE LEVEL | ☐ | ☐ | ☐ |
| • BELOW NORMAL PRE-DIALYSIS PLASMA CARNITINE LEVEL (<40-50 µmol/L) | ☐ | ☐ | ☐ |

RE-EVALUATE BY CLINICAL EXAM TO BE CERTAIN THAT THERAPIES GIVEN ARE ADEQUATE.

SIGNATURE _____ DATE _____    *NRT= NO RESPONSE TO THERAPY

FIG.9

MALAISE/FATIGUE

CHARTING TOOL

PATIENT NAME _____ I.D. # _____

AFTER RULING OUT MUSCLE WEAKNESS AS OUTLINED IN THE ALGORITHM, PROCEED AS FOLLOWS:

| RULE OUT SUPERIMPOSED NON-RENAL ILLNESS/CONDITION | YES | NO | NRT* |
|---|---|---|---|
| • DEPRESSION | ☐ | ☐ | ☐ |
| • CANCER | ☐ | ☐ | ☐ |
| • CONGESTIVE HEART FAILURE | ☐ | ☐ | ☐ |
| • THYROID DISEASE | ☐ | ☐ | ☐ |
| • COPD | ☐ | ☐ | ☐ |
| • UNCONTROLLED DIABETES | ☐ | ☐ | ☐ |
| • INFECTION | ☐ | ☐ | ☐ |
| • SEDATIVE DRUGS | ☐ | ☐ | ☐ |

| EVALUATE DIALYSIS SPECIFIC FACTORS | YES | NO | NRT* |
|---|---|---|---|
| • INADEQUATE DIALYSIS | ☐ | ☐ | ☐ |
|   – INAPPROPRIATE DIALYSIS WEIGHT | ☐ | ☐ | ☐ |
|   – UNDER-DIALYZED | | | |
| • INCOMPLETELY COMPENSATED ANEMIA (EPO DOSE ADJUSTED) | ☐ | ☐ | ☐** |
| • EVALUATE PRE-DIALYSIS PLASMA CARNITINE LEVEL | | ☐ | ☐ |
| • BELOW NORMAL PRE-DIALYSIS PLASMA CARNITINE LEVEL (<40–50 μmol/L) | | ☐ | ☐ |

** IF NO ADEQUATE RESPONSE SEE PATIENT DIAGNOSIS ALGORITHM FOR DELAYED/DIMINISHED RESPONSE TO EPO

RE-EVALUATE BY CLINICAL EXAM TO BE CERTAIN THAT THERAPIES GIVEN ARE ADEQUATE.

SIGNATURE _____ DATE _____

*NRT= NO RESPONSE TO THERAPY

FIG.11

DELAYED\DIMINISHED EPO RESPONSE                                                    CHARTING TOOL

PATIENT NAME _____  I.D. # _____

IF THE PATIENT FAILS TO RESPOND OR TO MAINTAIN A RESPONSE TO EPO DOSES WITHIN THE RECOMMENDED DOSING RANGE, EVALUATE/RECONSIDER
THE FOLLOWING ETIOLOGIES:

|  | YES | NO | NRT* |
|---|---|---|---|
| • IRON DEFICIENCY | ☐ | ☐ | ☐ |
| • UNDERLYING INFECTIOUS, INFLAMMATORY OR MALIGNANT PROCESS | ☐ | ☐ | ☐ |
| • OCCULT BLOOD LOSS | ☐ | ☐ | ☐ |
| • UNDERLYING HEMATOLOGIC DISEASE (I.E., THALASSEMIA, REFRACTORY ANEMIA OR OTHER MYELODYSPLASTIC DISORDERS) | ☐ | ☐ | ☐ |
| • HEMOLYSIS | ☐ | ☐ | ☐ |
| • OSTEITIS FIBROSA CYSTICA | ☐ | ☐ | ☐ |
| • ALUMINUM INTOXICATION | ☐ | ☐ | ☐ |
| • VITAMIN DEFICIENCIES (FOLIC ACID OR VITAMIN B12) | ☐ | ☐ | ☐ |
| • EVALUATE PRE-DIALYSIS PLASMA CARNITINE LEVEL | ☐ | ☐ | ☐ |
| • BELOW NORMAL PRE-DIALYSIS PLASMA CARNITINE LEVEL (<40-50 μmol/L) | ☐ | ☐ | ☐ |

RE-EVALUATE BY CLINICAL EXAM TO BE CERTAIN THAT THERAPIES GIVEN ARE ADEQUATE.

SIGNATURE _____ DATE _____  *NRT= NO RESPONSE TO THERAPY

FIG.13

DIALYSIS RELATED HYPOTENSION  CHARTING TOOL

PATIENT NAME _____ I.D. # _____

ACUTE EPISODE:

|  | YES | NO | NRT* |
|---|---|---|---|
| • TRENDELENBERG POSITION | ☐ | ☐ | ☐ |
| • IV FLUID | ☐ | ☐ | ☐ |
| • DECREASE OR ZERO UFR | ☐ | ☐ | ☐ |
| • CONSIDER OXYGEN | ☐ | ☐ | ☐ |
| • CONSIDER CAUSES AS IN CHRONIC SUSTAINED | ☐ | | |

CHRONIC SUSTAINED

|  | YES | NO | NRT* |
|---|---|---|---|
| • CARDIAC (ECHO) | ☐ | ☐ | ☐ |
| • PERICARDITIS | ☐ | ☐ | ☐ |
| • CHF | ☐ | ☐ | ☐ |
| • VALVE | ☐ | ☐ | ☐ |
| • ISCHEMIA | ☐ | ☐ | ☐ |
| • INFECTIONS | ☐ | ☐ | ☐ |
| • HEMOTOLOGIC | | ☐ | ☐ |
| • SEPSIS | | ☐ | ☐ |

RE-EVALUATE BY CLINICAL EXAM TO BE CERTAIN THAT THERAPIES GIVEN ARE ADEQUATE.

SIGNATURE _____ DATE _____ *NRT= NO RESPONSE TO THERAPY

FIG.15

CLINICAL MONITORING TOOL

PATIENT NAME _____  I.D. # _____

DIAGNOSIS: _____  DIALYSIS START DATE: _____

| | PARAMETER | BASELINE | ONE MONTH | THREE MONTHS | SIX MONTHS |
|---|---|---|---|---|---|
| CLINICAL LABORATORY | HEMOGLOBIN | | | | |
| | TRANS SATURATION | | | | |
| | RBC | | | | |
| | ALBUMIN | | | | |
| | GLUCOSE | | | | |
| | PHOSPHORUS | | | | |
| | BUN | | | | |
| | KT/V OR URR | | | | |
| | PRE-DIALYSIS PLASMA CARNITINE ($\mu$mol/L) | | | | |
| MEALS | EPO DOSAGE | | | | |
| | IRON DOSAGE | | | | |
| | CARNITOR R (LEVOCARNITINE) INJECTION DOSAGE | | | | |
| PATIENT ASSESSMENT | INTRADIALYTIC CRAMPING (FREQUENCY) | | | | |
| | HYPOTENSIVE EPISODES (FREQUENCY) | | | | |
| | SGA SCORE | | | | |
| | EJECTION FRACTION (%) | | | | |
| | APPETITE CHANGES | | | | |
| | FATIGUE | | | | |
| | PHYSICAL APPEARANCE | | | | |
| | HOSPITALIZATIONS (CHANGES IN FREQUENCY) | | | | |

CONTINUE THERAPY: YES ☐   NO ☐

SIGNATURE _____  DATE _____

FIG. 16

METHODS FOR THE DIAGNOSIS OF HEMODIALYSIS PATIENTS AND UTILIZATION OF SUCH METHODS TO IMPROVE THE ADMINISTRATION OF INTRAVENOUS LEVOCARNITINE TREATMENTS TO HEMODIALYSIS PATIENTS

CROSS REFERENCE TO RELATED APPLICATIONS

The present application claims priority from U.S. Provisional Patent Application Ser. No. 60/352,505, METHODS FOR THE DIAGNOSIS OF HEMODIALYSIS PATIENTS AND UTILIZATION OF SUCH METHODS TO IMPROVE THE ADMINISTRATION OF INTRAVENOUS LEVOCARNITINE TREATMENTS TO HEMODIALYSIS PATIENTS, filed Jan. 31, 2002, which is hereby incorporated by reference. Furthermore, the present application is related in subject matter to U.S. Pat. No. 6,335,369, TREATING CHRONIC UREMIC PATIENTS UNDERGOING PERIODICAL DIALYSIS, issued Jan. 1, 2002, the specification of which is hereby incorporated by reference in its entirety.

FIELD OF THE INVENTION

The present invention relates to methods for diagnosing and treating various conditions prevalent in hemodialysis patients with end stage renal disease. In particular, the present invention pertains to methods for diagnosing clinical conditions that are common in hemodialysis patients and that may be related to abnormal carnitine metabolism resulting from hemodialysis; thus, the present invention provides methods for monitoring and improving the administration of therapeutic intravenous levocarnitine to such patients.

BACKGROUND OF THE INVENTION

Studies indicate that more than 70% of the carnitine present in the plasma of a hemodialysis patient can be removed during a dialysis session. Carnitine is a naturally occurring substance in the human body required for energy metabolism at the cellular level because it transports fatty acid-derivatives into the inner aspect of the mitochondrionia to produce energy and removes various acyl moeities from the mitochondria and cells. Dialytic loss of carnitine by patients undergoing hemodialysis is thought to be attributable to the compound's relatively small molecular weight, high water solubility, and poor protein binding. Carnitine levels are further diminished in end stage renal disease patients by reduced renal synthesis and reduced intake of meat and dairy foods.

Primary and secondary carnitine deficiency syndromes are well-described entities whose clinical sequelae could result in serious illness or death. Carnitine deficiency syndromes are characterized by such diverse symptoms as cardiomyopathy, muscle weakness, lipid storage myopathy, hepatic dysfunction, encephalopathy, failure to thrive, and recurrent infections.

As described in U.S. Pat. No. 6,335,369, the administration of levocarnitine may be beneficially used to treat carnitine deficiency in patients with end stage renal disease ("ESRD") who are undergoing regular hemodialysis. Chronic uremic patients undergoing periodical hemodialysis are treated with carnitine or one of its salts to prevent or treat carnitine deficiency in patients with end stage renal disease. An effective dose of levocarnitine (the recommended starting intravenous dosage is typically 10-20 mg of drug per kg of patient dry body weight) is administered intravenously via a venous return line after each dialysis session. Initiation of such levocarnitine injection therapy may be prompted by pre-dialysis plasma free carnitine concentrations that are below normal (normal concentrations being approximately 40-50 micromoles/liter ($\mu$mol/L)). Such intravenous administration of levocarnitine to end stage renal disease patients on hemodialysis results in increased plasma carnitine concentrations and thereby makes it possible to correct for the loss of plasma carnitine which otherwise takes place during hemodialysis therapy. Importantly, immediately after giving intravenous carnitine to a patient at the end of a dialysis session, carnitine levels in the patient's plasma rise to high levels and then return to a pre-dialysis baseline levels after approximately 10-24 hours (presumably because the carnitine has entered the tissues). In this manner, it is possible to avoid tissue carnitine depletion, which is a long-term consequence of repeated losses of carnitine from plasma that the patient undergoes during successive dialytic sessions over a prolonged period of time.

Prior studies have listed specific subsets of patients in whom intravenously administered carnitine had been associated with improvement in clinical parameters. These subsets of patients have included those with cardiomyopathy, skeletal muscle weakness/myopathy, anemia of uremia unresponsive to or requiring large doses of erythropoietin (EPO), lack of energy (which has a negative effect upon quality of life), severe and persistent muscle cramps, and/or intradialytic hypotensive episodes. Despite these studies, the use of levocarnitine in dialysis patients is sometimes limited.

Cardiomyopathy, muscle weakness, and fatigue are often due to factors other than carnitine deficiency. The ability to methodically analyze these common conditions is critical to the appropriate application of this therapy. Non-critical use of carnitine is both medically incorrect and economically wasteful. Thus, there remains a need in the art for methods to differentiate other etiologies for clinical conditions that have been associated with dialysis related carnitine deficiency and for which intravenous levocarnitine therapy is being considered in the treatment of dialysis patients.

SUMMARY OF THE INVENTION

In light of the above-described and other deficiencies, the present invention as disclosed herein is intended to help health care professionals in the diagnosis of ESRD patients undergoing dialysis with diagnosing clinical conditions and symptoms that are common in hemodialysis patients and to help document the medical necessity of selected treatments. Clinical algorithms have been developed for the clinical symptoms seen in ESRD patients that may be related to camitine deficiency. These symptoms include secondary cardiomyopathy, dialysis related hypotension, cardiac arrhythmia, muscle wasting or weakness, muscle cramping, protein catabolism, lack of energy, and delayed or diminished response to erythropoietin ("EPO"). Monitoring tools to assist health care professionals in implementing the clinical algorithms are also provided.

ESRD patients with the above conditions, as well as those with poor erythropoietin response, who have demonstrated an inadequate response to appropriate therapy are prescribed a course of intravenous levocarnitine in a recommended range of drug dose and duration of therapy. Once patients have been on this therapy in recommended dose and duration a clinical outcome monitoring tool is used to evaluate a response.

Embodiments of the present invention provide methods for monitoring and improving the administration of therapeutic levocarnitine to ESRD patients by providing clinical algorithms and accompanying tools that are adapted to assist health care professionals in assessing patient status from such symptoms and identifying appropriate therapeutic actions to take. These methods can also be incorporated as a computer-based software application that records the data for individual patents and systematically guides the health care practitioner through the required steps.

BRIEF DESCRIPTION OF THE DRAWINGS

FIG. 3 is an example of a charting tool for implementing a cardiomyopathy clinical algorithm according to the embodiments of the present invention.

FIG. 5 is an example of a charting tool for implementing a cardiac arrhythmias clinical algorithm according to the embodiments of the present invention.

FIG. 7 is an example of a charting tool for implementing a muscle weakness clinical algorithm according to the embodiments of the present invention.

FIG. 9 is an example of a charting tool for implementing a muscle myopathy clinical algorithm according to the embodiments of the present invention.

FIG. 11 is an example of a charting tool for implementing a malaise/fatigue clinical algorithm according to the embodiments of the present invention.

FIG. 13 is an example of a charting tool for implementing a delayed or diminished EPO response clinical algorithm according to the embodiments of the present invention.

FIG. 15 is an example of a charting tool for implementing a dialysis related hypotension clinical algorithm according to the embodiments of the present invention.

FIG. 16 is an example of a clinical outcome monitoring tool to track a patient's response to levocarnitine therapy according to the embodiments of the present invention.

DETAILED DESCRIPTION OF THE PREFERRED EMBODIMENTS

As shown in FIGS. 1-16, embodiments of the present invention are methods that help health care professionals to associate common symptoms identified in end stage renal disease ("ESRD") patients with one or more appropriate diagnosing algorithms and their associated tools for monitoring and improving the potential administration of therapeutic levocarnitine to such patients.

Figure 1:
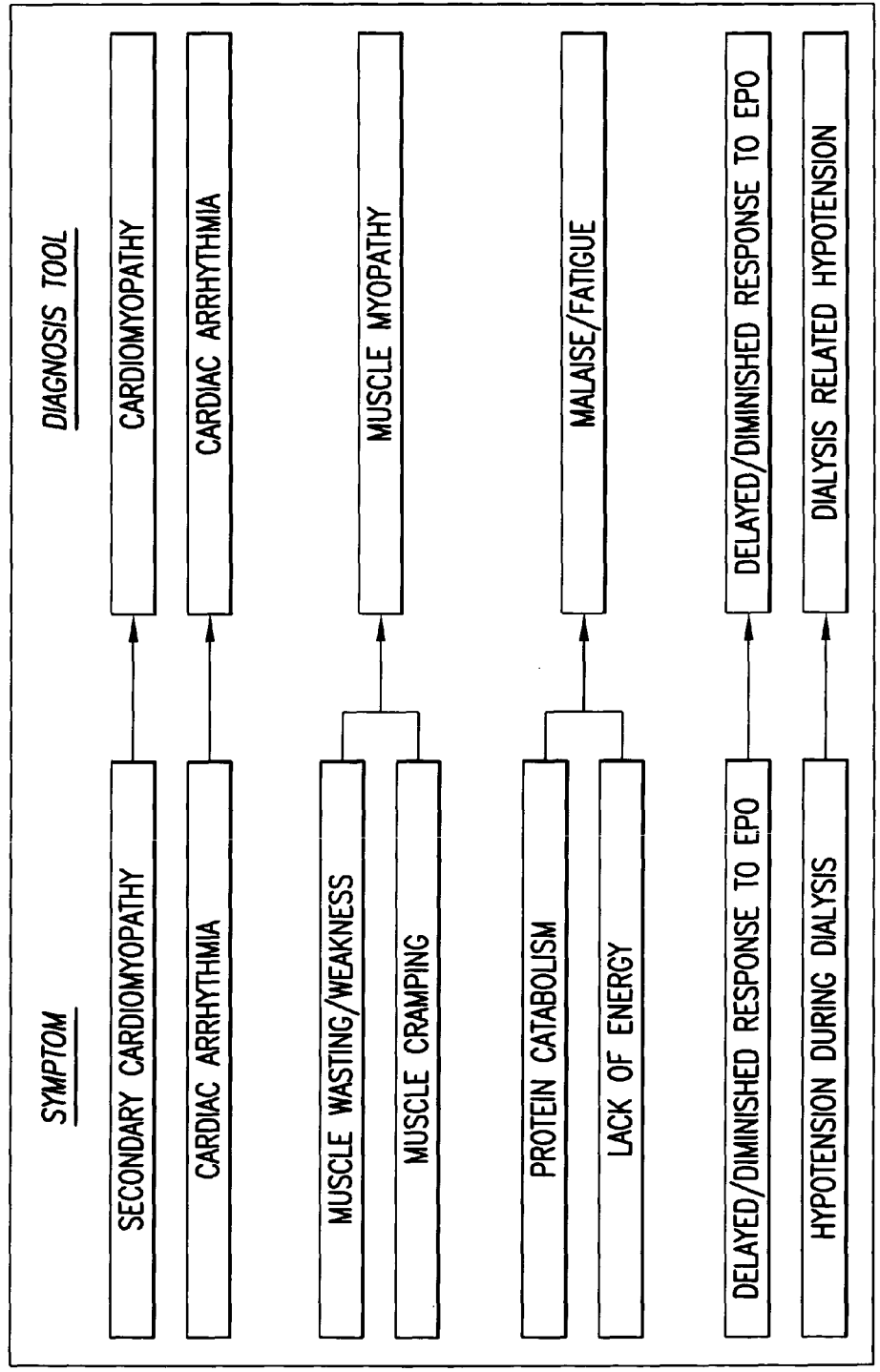
FIG. 1 is a schematic diagram depicting the basic patient symptoms and associated diagnostic modules of the present invention.

As shown in FIG. 1, symptoms can be associated with one of six diagnosing algorithm and tool sets, namely, the pairs for cardiomyopathy (FIGS. 2a-3), cardiac arrhythmia (FIGS. 4-5), muscle myopathy (FIGS. 6-9), malaise/fatigue (FIGS. 10-11), delayed/diminished response to EPO (FIGS. 12-13), and dialysis related hypotension (FIGS. 14-16). In use, a health care professional applies the appropriate diagnosing algorithm (for example, the cardiomyopathy algorithm of FIG. 2a) depending upon the symptom(s) (e.g., secondary cardiomyopathy) presented by the ESRD patient to determine the patient's status and potential suitability for levocarnitine administration. Additionally, the health care professional concurrently with the application of the diagnosing algorithm uses the appropriate monitoring and treatment tool (in the case of the above example, the cardiomyopathy tool illustrated by FIG. 3) to record the patient's response to the diagnostics (and, potentially, treatments) performed according to the related diagnosing algorithm (i.e., FIG. 2a for cardiomyopathy). FIGS. 2a-16 describe the application of the diagnosing algorithms and tools according to the invention in detail.

Figure 2A:
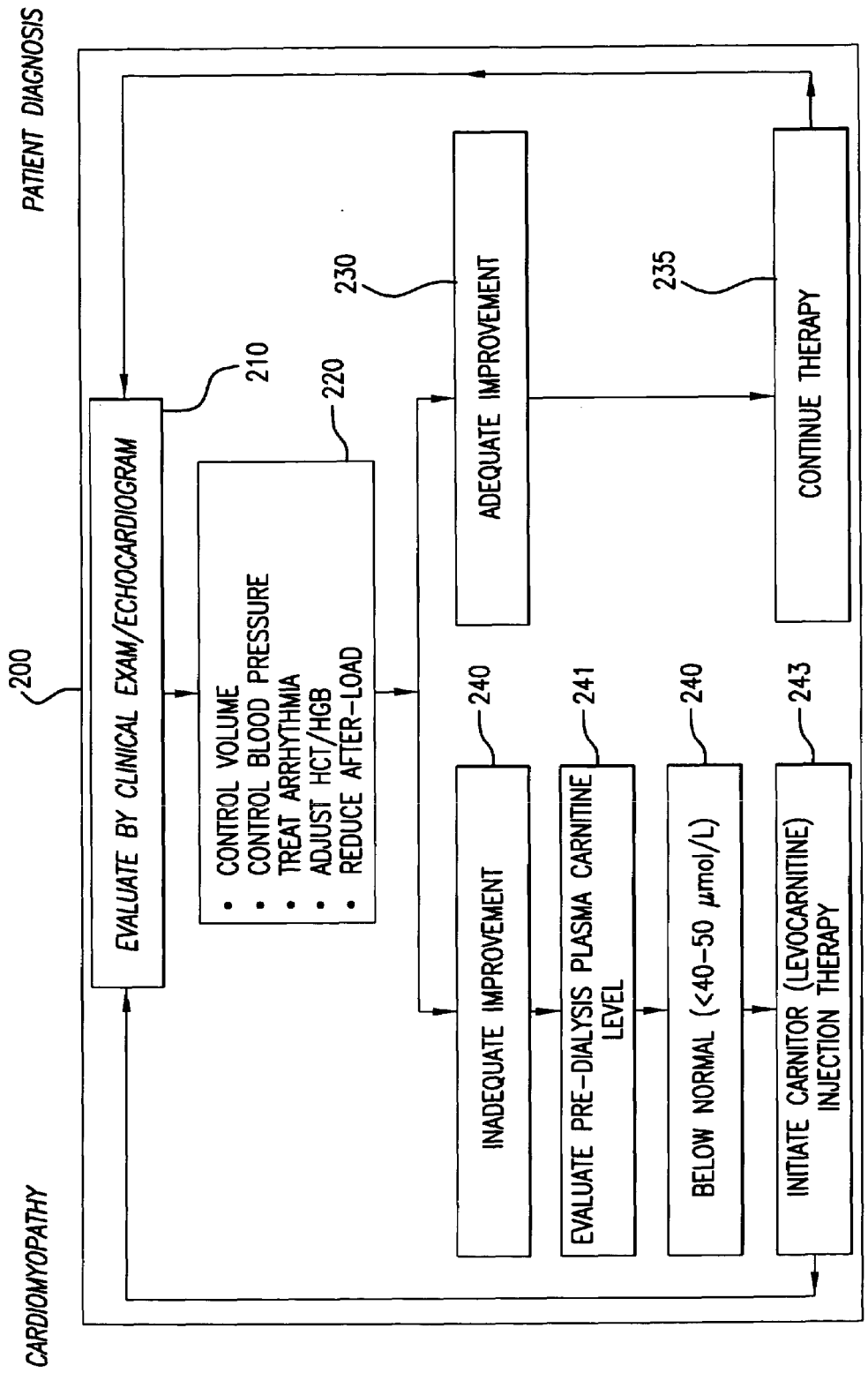
FIG. 2a is a schematic diagram depicting the steps for a cardiomyopathy diagnostic module.

FIG. 2a depicts the appropriate diagnosing algorithm for cardiomyopathy 200 to determine a patient's status and potential suitability for levocarnitine administration given the symptoms of secondary cardiomyopathy as shown in FIG. 1. According to the algorithm in FIG. 2, a patient with these symptoms is evaluated by clinical exam 210 and considered for a series of treatments 220 known to those skilled in the art that include controlling fluid volume during dialysis, controlling blood pressure, treating arrhythmia, adjusting hematocrit (HCT)/hemoglobin (HGB), and reducing after-load. If these treatments provide adequate improvement upon evaluation 230, then they are continued 235, and the patient will continue to be monitored in subsequent clinical exams 210. If the treatments 220 do no provide adequate improvement upon evaluation 240, then the health care professional will evaluate the patient's pre-dialysis plasma carnitine concentration 241, determine if the pre-dialysis carnitine level is below normal 242, and, if so, initiate levocarnitine injection therapy 243. The steps of algorithm 200 are charted in FIG. 3, such that a health care professional can effectively monitor the diagnostic process.

Figure 2B:
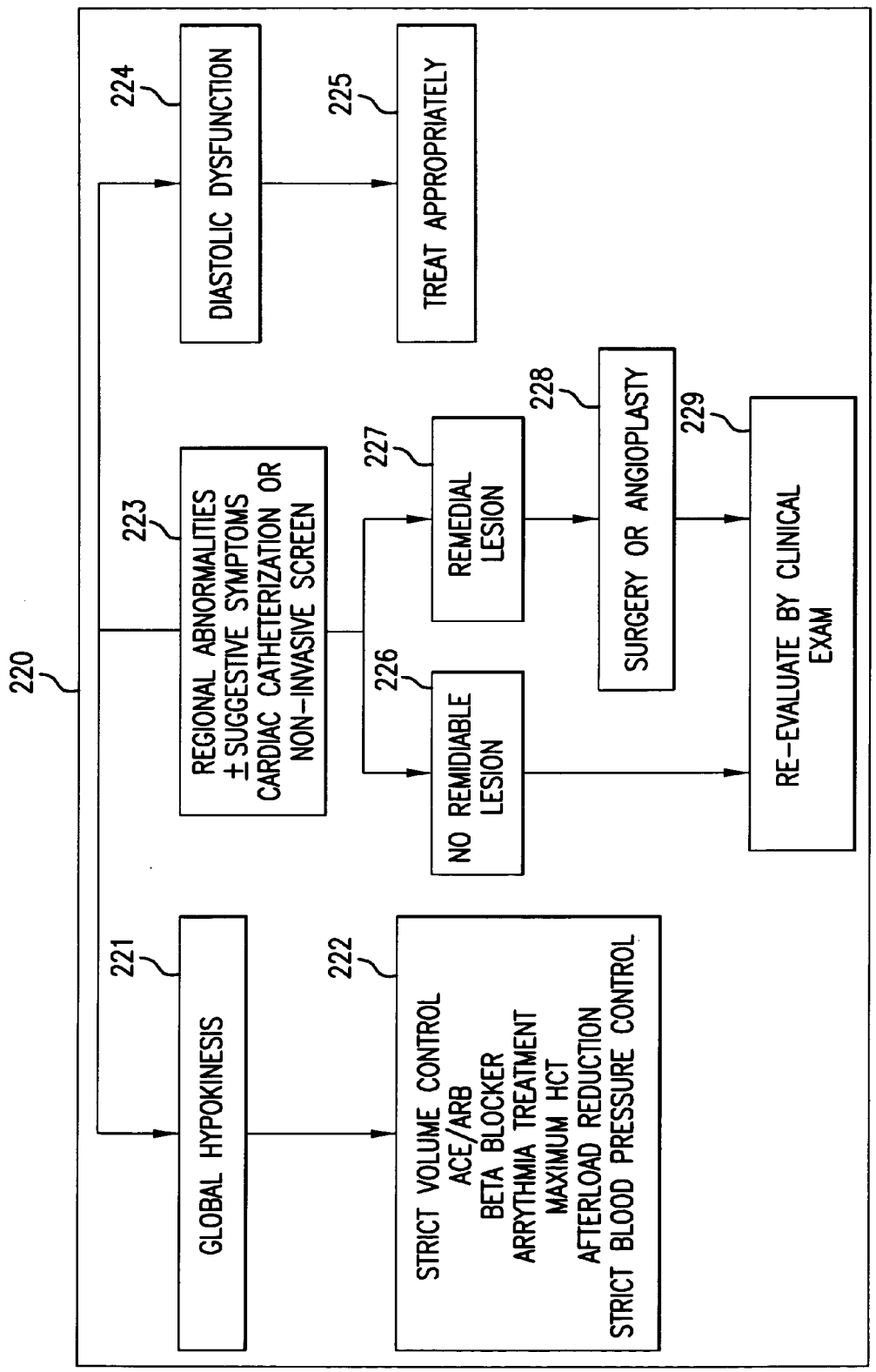
FIG. 2b is a schematic diagram depicting alternate steps for a cardiomyopathy diagnostic module according to one embodiment of the invention.

In one embodiment of the appropriate diagnosing algorithm for cardiomyopathy 200, step 220 is made of additional steps as depicted in FIG. 2b. One step is considering the possibility of global Hypokinesis 221, and if present, implementing appropriate treatments such as strict volume control, angiotensin-converting enzyme (ACE) and angiotensin receptor blocker (ARB) treatments, beta blocker treatment, arrhythmia treatment, maximum HCT, (not to be excessive), afterload reduction, or strict blood pressure control. Another step is determining if there may be a diastolic dysfunction 224, and if so, treating appropriately 225. An additional step is determining if regional abnormalities are present with/without suggestive symptoms through a cardiac catheterization or non-invasive screen 223. If a remedial lesion 227 is found, then surgery or angioplasty 228 is required. If no remedial lesion is found 226, then the patient is re-evaluated by clinical exam 229.

Figure 4:
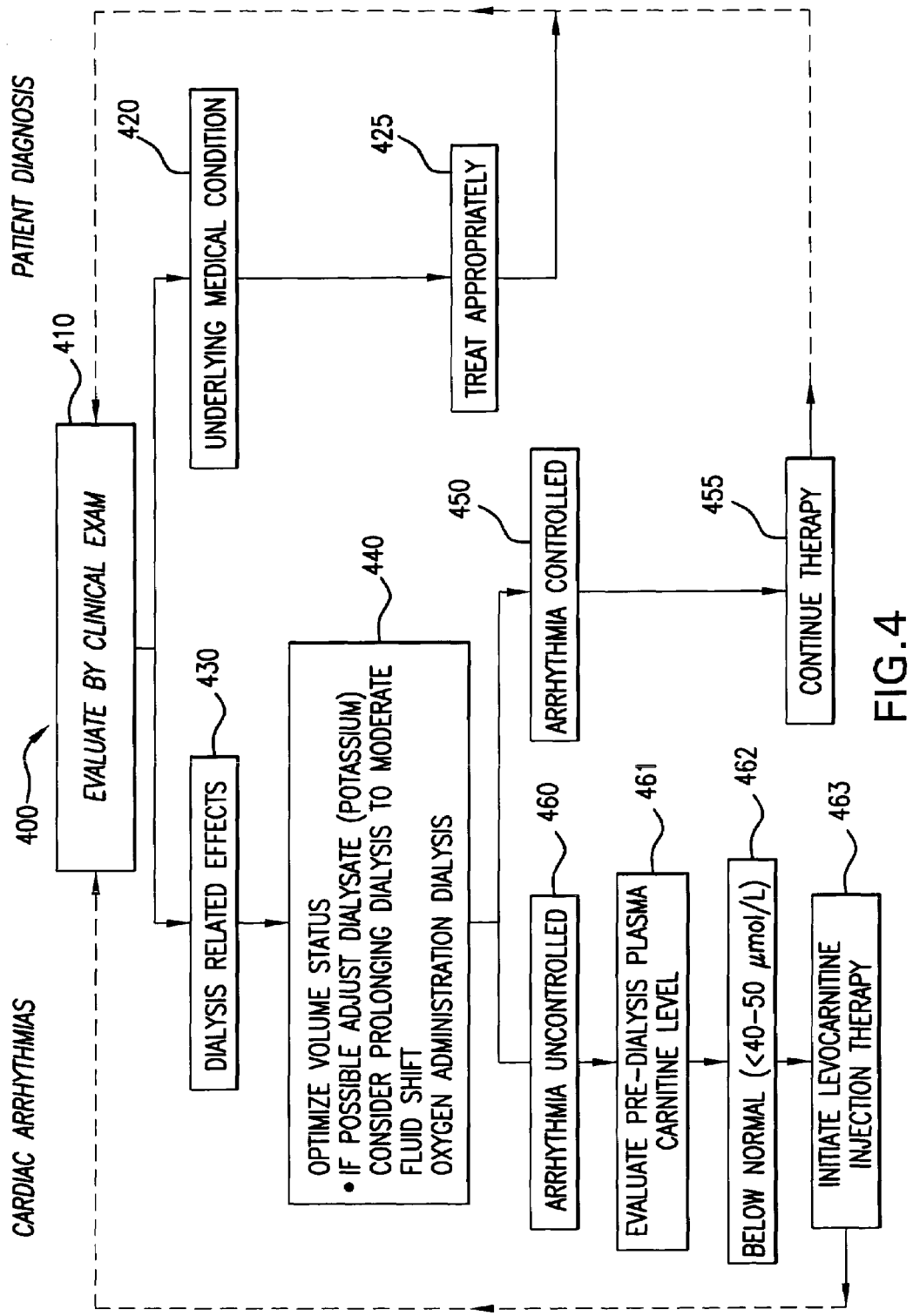
FIG. 4 is a schematic diagram depicting the steps for a cardiac arrhythmias diagnostic module.

FIG. 4 depicts the appropriate diagnosing algorithm 400 to determine a patient's status and potential suitability for levocarnitine administration given the symptoms of cardiac arrhythmia as shown in FIG. 1. According to the algorithm in FIG. 4, a patient with these symptoms is evaluated by clinical exam 410, and the health care professional determines whether the symptoms are related to an underlying medical condition 420 or are related to effects from dialysis 430. If the arrhythmia symptoms are related to an underlying medical condition, then appropriate treatment 425 relating to the underlying condition must first be provided, and the patient will continue to be monitored in subsequent clinical exams 410. If the arrhythmia symptoms are determined to be related to dialysis treatment 430, a series of adjustments to the dialysis process 440 known to those skilled in the art are considered that include optimizing the volume status, adjusting the dialysate if possible, prolonging dialysis to moderate fluid shifts, and administering oxygen during dialysis. If these changes to the dialysis process control the arrhythmia symptoms upon evaluation 450, then they are continued 455, and the patient will continue to be monitored in subsequent clinical exams 410. If changes to the dialysis process do not control the arrhythmia symptoms 450, then the health care professional will evaluate the patient's pre-dialysis plasma carnitine concentration 461, determine if the pre-dialysis carnitine level is below normal 462, and, if so, initiate levocarnitine injection therapy 463. The steps of algorithm 400 are charted in FIG. 5, such that a health care professional can effectively monitor the diagnostic process.

Figure 6:
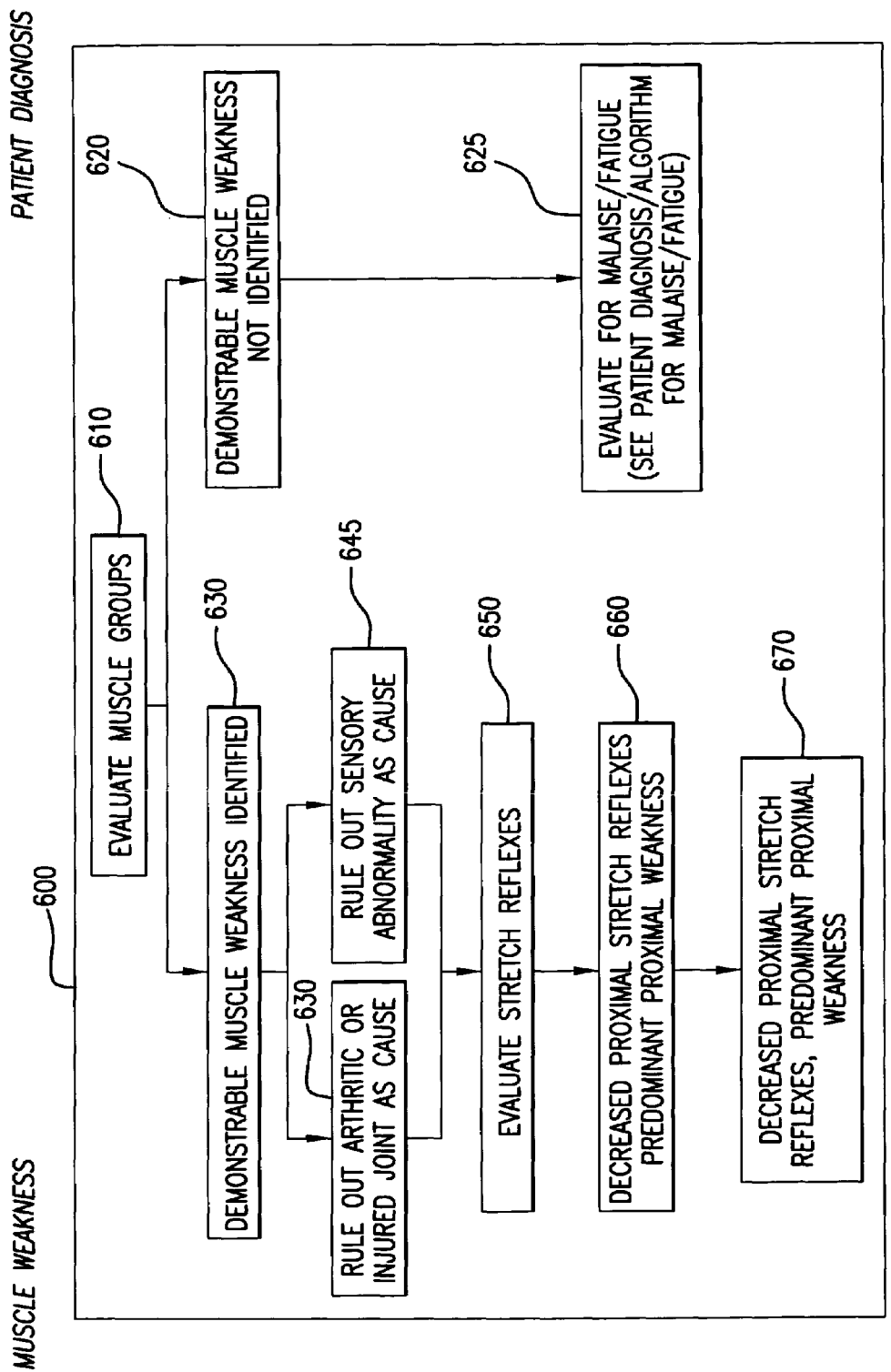
FIG. 6 is a schematic diagram depicting the steps for a muscle weakness diagnostic module.

FIG. 6 depicts the appropriate diagnosing algorithm 600 to determine a patient's status and potential suitability for levocarnitine administration given the symptoms of muscle weakness as shown in FIG. 1. Different clinical algorithms are available for symptoms of muscle weakness, as compared to symptoms of general fatigue. According to the algorithm in FIG. 6, a health care professional examines the muscle groups of a patient with these symptoms 610 to determine if the patient exhibits demonstrable muscle weakness. If no demonstrable muscle weakness is identified 620, then the patient is evaluated for malaise/fatigue 625 in accordance with the steps of FIG. 10. If demonstrable muscle weakness is identified 630, then the health care professional must rule out the possible effects of an arthritic or injured joint 640 or a sensory abnormality 645 as the cause of the apparent muscle weakness before proceeding to further evaluation. If there are no sensory abnormalities or joint weakness, then the stretch reflexes of the patient are evaluated 650. If the evaluation shows decreased proximal stretch reflexes or predominant proximal weakness, then the patient is evaluated for muscle myopathy 670 in accordance with the steps of FIG. 8. The steps of algorithm 600 are charted in FIG. 7, such that a health care professional can effectively monitor the diagnostic process.

Figure 8:
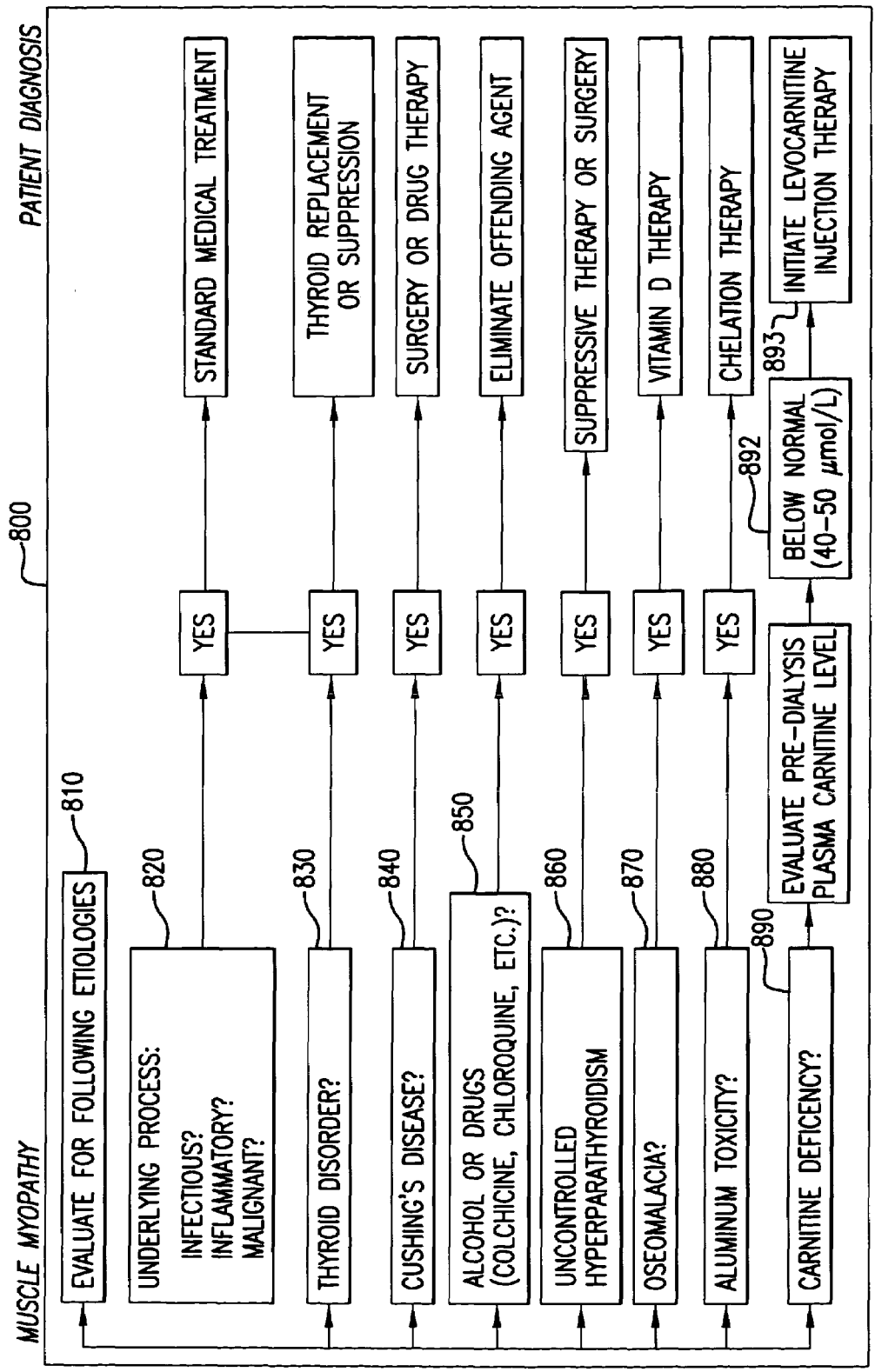
FIG. 8 is a schematic diagram depicting the steps for a muscle myopathy diagnostic module.

FIG. 8 depicts the appropriate diagnosing algorithm 800 to determine a patient's status and potential suitability for levocarnitine administration given the symptoms of muscle weakness/wasting or muscle cramping as shown in FIG. 1. According to the algorithm in FIG. 8, a patient with these symptoms is evaluated by clinical exam 810, to determine the cause or origin of the muscle cramping of the demonstrated muscle weakness beyond the evaluation of FIG. 6. The health care professional must rule out the possible symptoms of muscle myopathy unrelated to dialysis before proceeding to further evaluation of possible carnitine deficiency.

Reviewing the steps in FIG. 8, possible acquired infection, inflammation, or malignancy 820 must be considered and, if present, treated using skills known in the art. Also, thyroid disorders 830 must be considered and, if present, treated accordingly. Furthermore, Cushing's disease 840 must be considered and, if present, treated with appropriate drug therapy or surgery as determined by the health care professional. Additionally, alcohol or drug use 850 may be the cause of the muscle myopathy symptoms, and, if so, the use of the offending agent must be eliminated. Uncontrolled hyperparathyroidism 860 is yet another possibly cause that must be considered, and if present, treated appropriately with suppressive therapy or surgery. Also, osteomalacia 870 must be considered and, if present, treated with appropriate treatment such as vitamin D therapy. Moreover, aluminum toxicity 880 must be considered as a possible cause of muscle myopathy, and, if present, treated with appropriate means such as chelation therapy. Finally, if none of the previous etiologies are present, a carnitine deficiency 890 is a likely cause of muscle myopathy symptoms. As shown in FIG. 8, the health care professional will evaluate the patient's pre-dialysis plasma carnitine concentration 891, determine if the pre-dialysis carnitine level is below normal 892, and, if so, initiate levocarnitine injection therapy 893. The steps of algorithm 800 are charted in FIG. 9, such that a health care professional can effectively monitor the diagnostic process.

Figure 10:
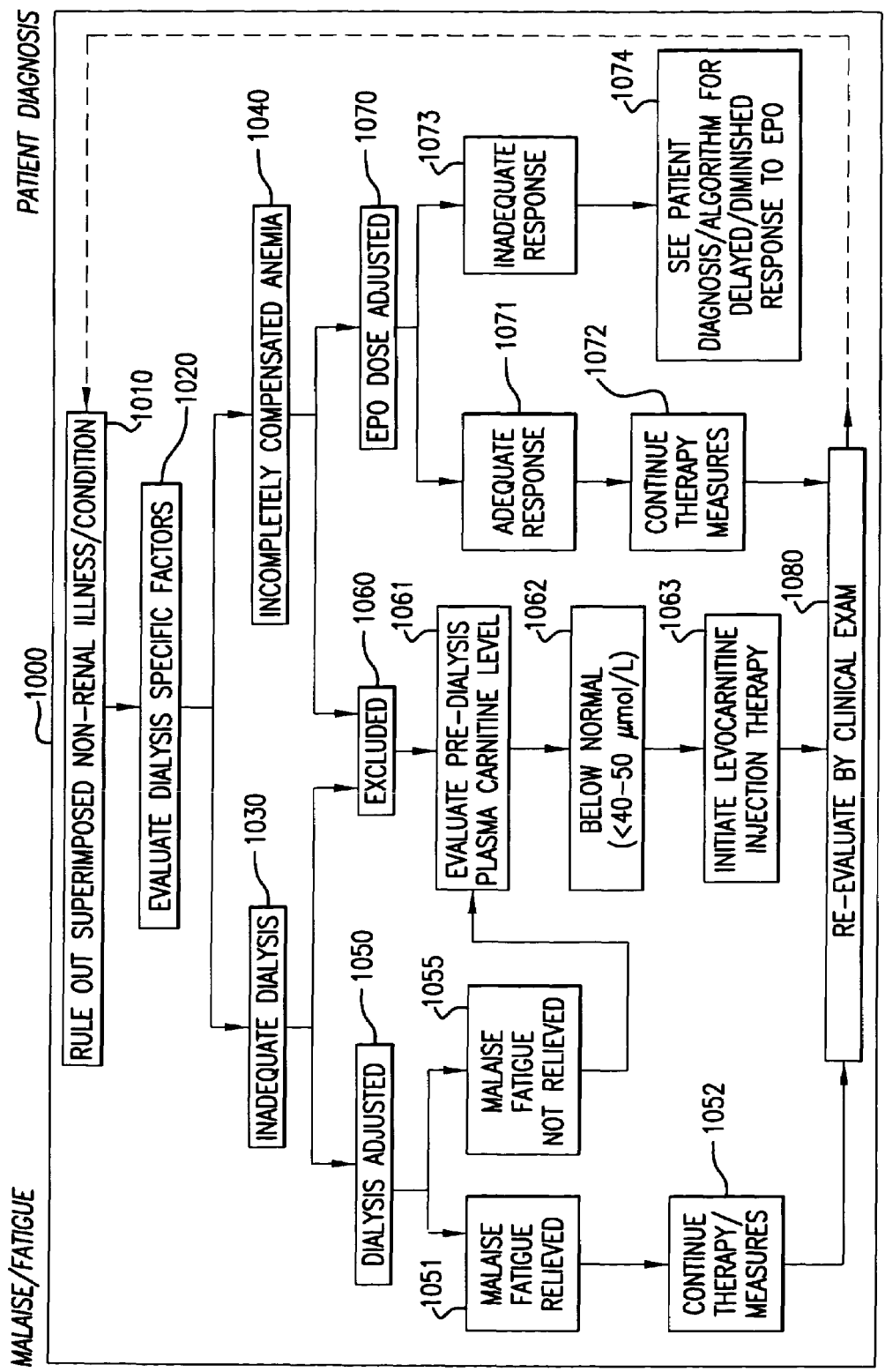
FIG. 10 is a schematic diagram depicting the steps for a malaise/fatigue diagnostic module.

FIG. 10 depicts the appropriate diagnosing algorithm 1000 to determine a patient's status and potential suitability for levocarnitine administration given the symptoms of protein catabolism or lack of energy as shown in FIG. 1. According to the algorithm in FIG. 10, a patient with these symptoms is evaluated by clinical exam 1010 to rule out a non-renal illness or condition as the cause or origin of the symptoms before evaluating factors specific to dialysis 1020. The health care professional must consider inadequate dialysis 1030 and incompletely compensated anemia 1040 as possible causes of a patients symptoms of malaise or fatigue. If both inadequate dialysis 1030 and incompletely compensated anemia 1040 are excluded as possible causes 1060, then the health care professional will evaluate the patient's pre-dialysis plasma carnitine concentration 1061, determine if the pre-dialysis carnitine level is below normal 1062, and, if so, initiate levocarnitine injection therapy 1063.

Still referring to FIG. 10, if inadequate dialysis 1030 is a possible cause of the malaise or fatigue symptoms, the dialysis must be adjusted 1050. If the adjusted dialysis 1050 relives the symptoms of malaise or fatigue 1051, then the successful measures should be continued 1052 and the patient re-evaluated as necessary 1080. If the adjusted dialysis 1050 does not relieve the symptoms of malaise or fatigue 1055, then the health care professional will evaluate the patient's pre-dialysis plasma carnitine concentration 1061, determine if the pre-dialysis carnitine level is below normal 1062, and, if so, initiate levocarnitine injection therapy 1063. If incompletely compensated anemia 1040 is a possible cause of the malaise or fatigue symptoms, the EPO dose must be adjusted 1070. If the adjusted EPO dose 1070 produces an adequate response (e.g., relives the symptoms of malaise or fatigue) 1071, then the successful measures should be continued 1072 and the patient reevaluated as necessary 1080. If the adjusted EPO dose 1070 produces an inadequate response (e.g., does not relive the symptoms of malaise or fatigue) 1073, then the patient is evaluated for delayed/diminished response to EPO 1074 in accordance with the steps of FIG. 12. The steps of algorithm 1000 are charted in FIG. 11, such that a health care professional can effectively monitor the diagnostic process.

Figure 12:
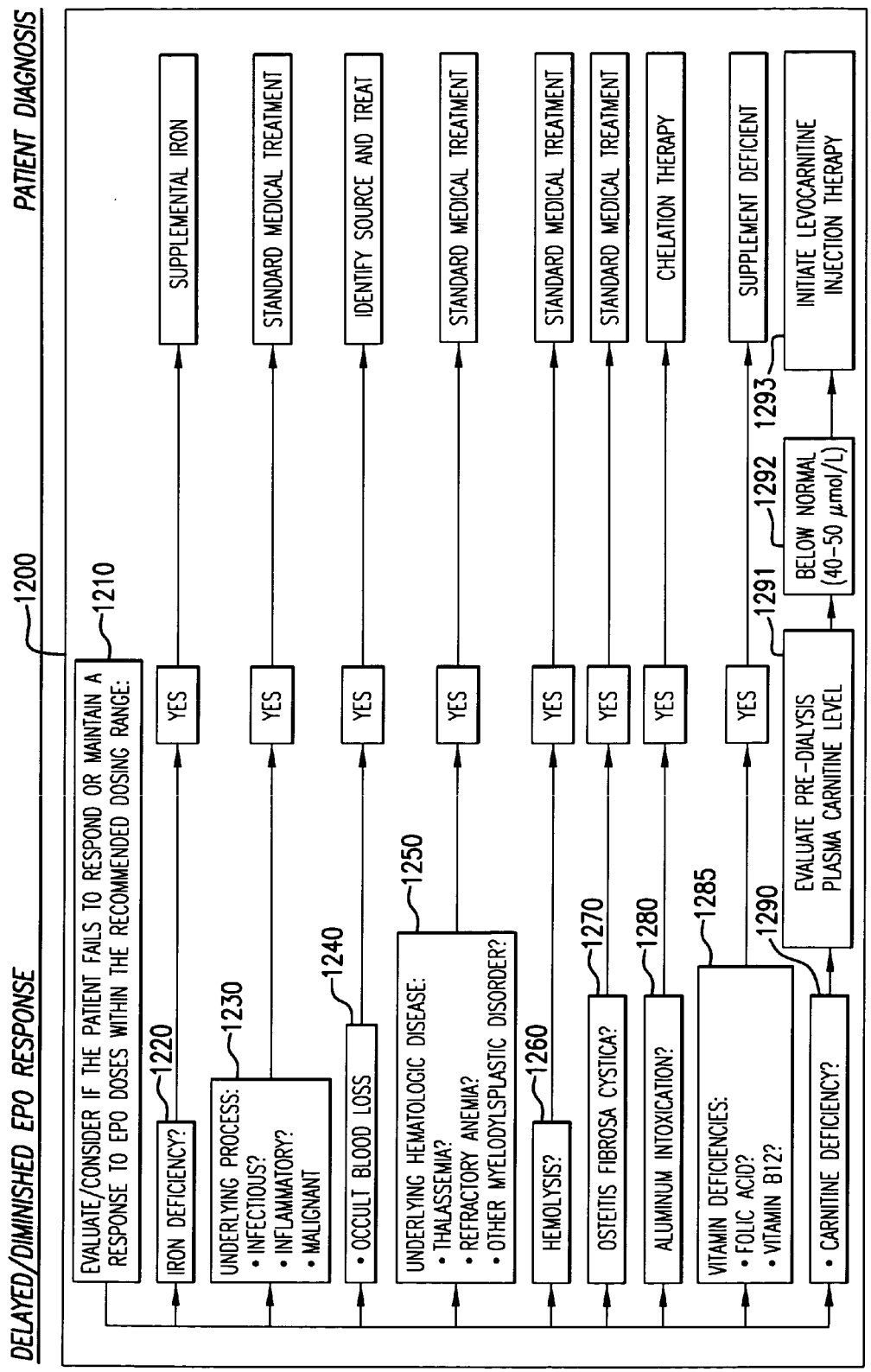
FIG. 12 is a schematic diagram depicting the steps for a delayed or diminished erythropoietin ("EPO") response diagnostic module.

FIG. 12 depicts the appropriate diagnosing algorithm 1200 to determine a patient's status and potential suitability for levocarnitine administration given the symptoms of delayed or diminished response to EPO as shown in FIG. 1. According to the algorithm in FIG. 12, a patient is evaluated by clinical exam 1210 to rule out symptoms of delayed or diminished response to EPO that are unrelated to reduced carnatine levels before proceeding to further evaluation of possible carnitine deficiency.

Reviewing the steps in FIG. 12, iron deficiency 1220 must be considered and, if present, treated accordingly with, for example, supplemental iron. Also, possible acquired infection, inflammation, or malignancy 1230 must be considered and, if present, treated using skills known in the art. Furthermore, occult blood loss 1240 must be considered and, if present, the source of bleeding identified and treated with appropriate measures. Additionally, an underlying hematologic disease 1250, such as thalassemia, refractory anemia, or other myelodysplastic disorders, may be the cause of the delayed or diminished response to EPO symptoms, and, if so, these diseases must be treated accordingly. Hemolysis 1260 is yet another possibly cause that must be considered, and if present, treated appropriately. Also, osteitis fibrosa cystica 1270 must be considered and, if present, treated with standard medical treatment. Moreover, aluminum intoxication 1280 must be considered as a possible cause of delayed or diminished response to EPO, and, if present, treated with appropriate means such as chelation therapy. Likewise, vitamin deficiencies 1285, such as a lack of folic acid or vitamin B12, must be considered and, if present, treated accordingly with, for example, supplemental vitamins. Finally, if none of the previous indications are present, a carnitine deficiency 1290 is a likely cause of the delayed or diminished response to EPO symptoms. As shown in FIG. 12, the health care professional will evaluate the patient's pre-dialysis plasma carnitine concentration 1291, determine if the pre-dialysis carnitine level is below normal 1292, and, if so, initiate levocarnitine injection therapy 1293. The steps of algorithm 1200 are charted in FIG. 13, such that a health care professional can effectively monitor the diagnostic process.

Figure 14A:
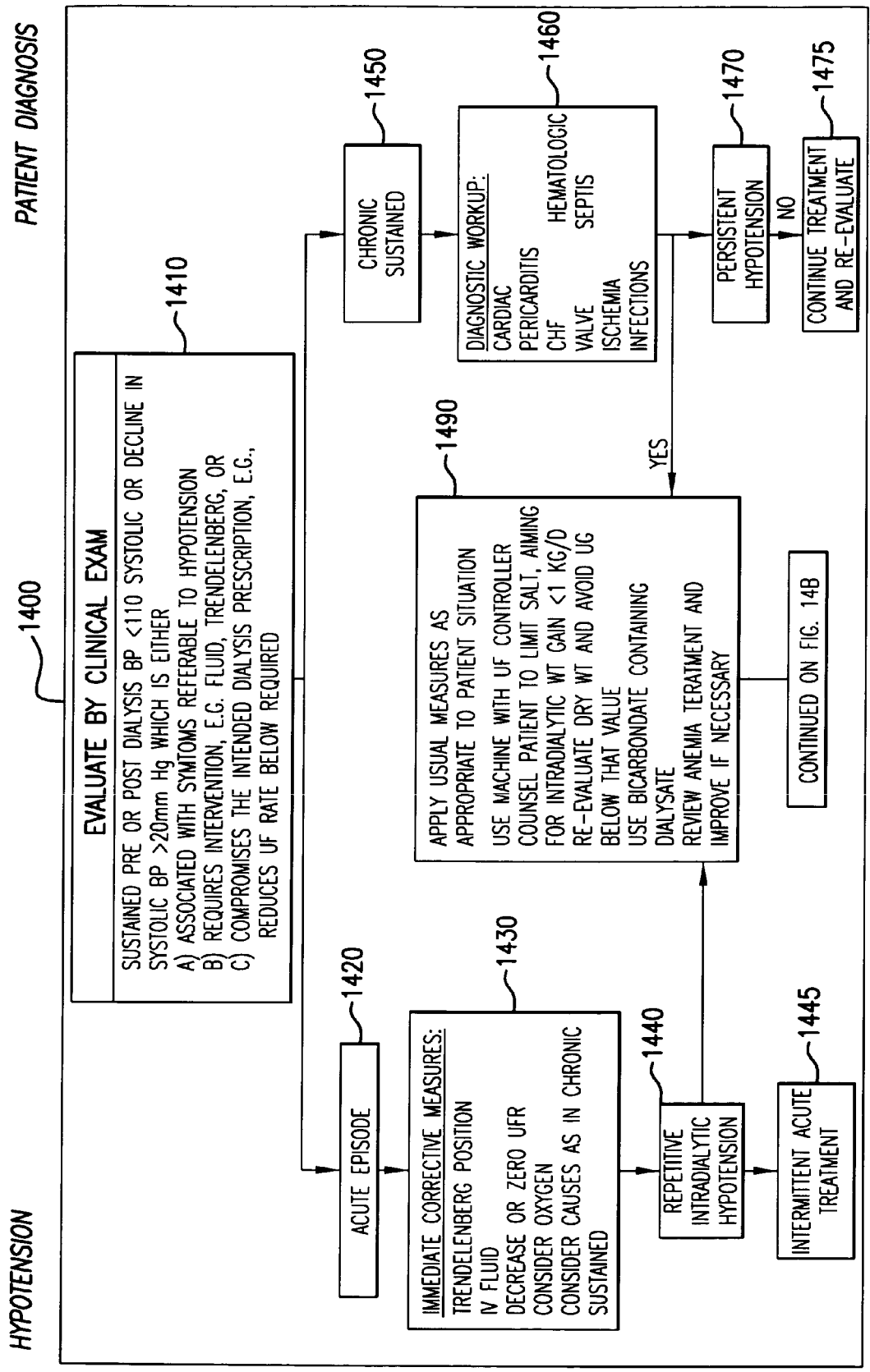
FIG. 14a is part one of a schematic diagram depicting the steps for a dialysis related hypotension diagnostic module.

FIG. 14a depicts the appropriate diagnosing algorithm 1400 to determine a patient's status and potential suitability for levocarnitine administration given the symptoms of dialysis related hypotension as shown in FIG. 1. According to the algorithm in FIG. 14a, a patient with these symptoms is evaluated by clinical exam 1410 for hypotension (e.g., sustained pre- or post-dialysis blood pressure less than 110 systolic or a decline in systolic blood pressure greater than 20 mm Hg which is either (a) associated with symptoms referable to hypotension, (b) requires intervention, or (c) compromises the intended dialysis prescription). From the examination 1410, the health care professional determines whether the symptoms of hypotension are an acute episode 1420 or a chronic sustained condition 1450. If the symptoms indicate an acute episode 1420, then the health care professional initiates immediate corrective measures 1430, such as repositioning said the patient into a Trendelenberg position, using IV fluid, decreasing or zeroing ultrafiltration rate (UFR) for the dialysis, considering use of oxygen, or considering the causes as in chronic sustained step 1450. If the acute episode is not indicative of repetitive intradialytic hypotension, then intermittent acute treatment is continued 1445. If the acute episode 1420 is indicative of repetitive intradialytic hypotension, then the health care professional must apply initial measures 1490 known to those skilled in the art as appropriate to the patient's situation, such as using a machine with ultrafiltration control, counseling patient to limit salt, aiming for intradialytic weight gain greater than 1 kg/d, re-evaluating dry weight and avoiding ultrafiltration below that value, using bicarbonate containing dialysate, and reviewing anemia treatment to see if improvements are necessary.

Continuing with FIG. 14a, if the symptoms are a chronic sustained condition 1440, then the health care professional conducts a series of diagnostics 1450, including electrocardiograms, evaluating for pericarditis, testing for congestive heart failure (CHF), considering possible valve problems, checking for ischemia, testing for infections, considering hematologic disorders, and evaluating for sepsis. If the diagnostics 1450 indicate persistent hypotension despite treatment of the underlying condition, then the health care professional must apply initial measures 1490 known to those skilled in the art as appropriate to the patient's situation. If the diagnostics 1450 indicate hypotension is related to the underlying condition, then the treatment of the underlying condition is continued 1475, as necessary.

Figure 14B:
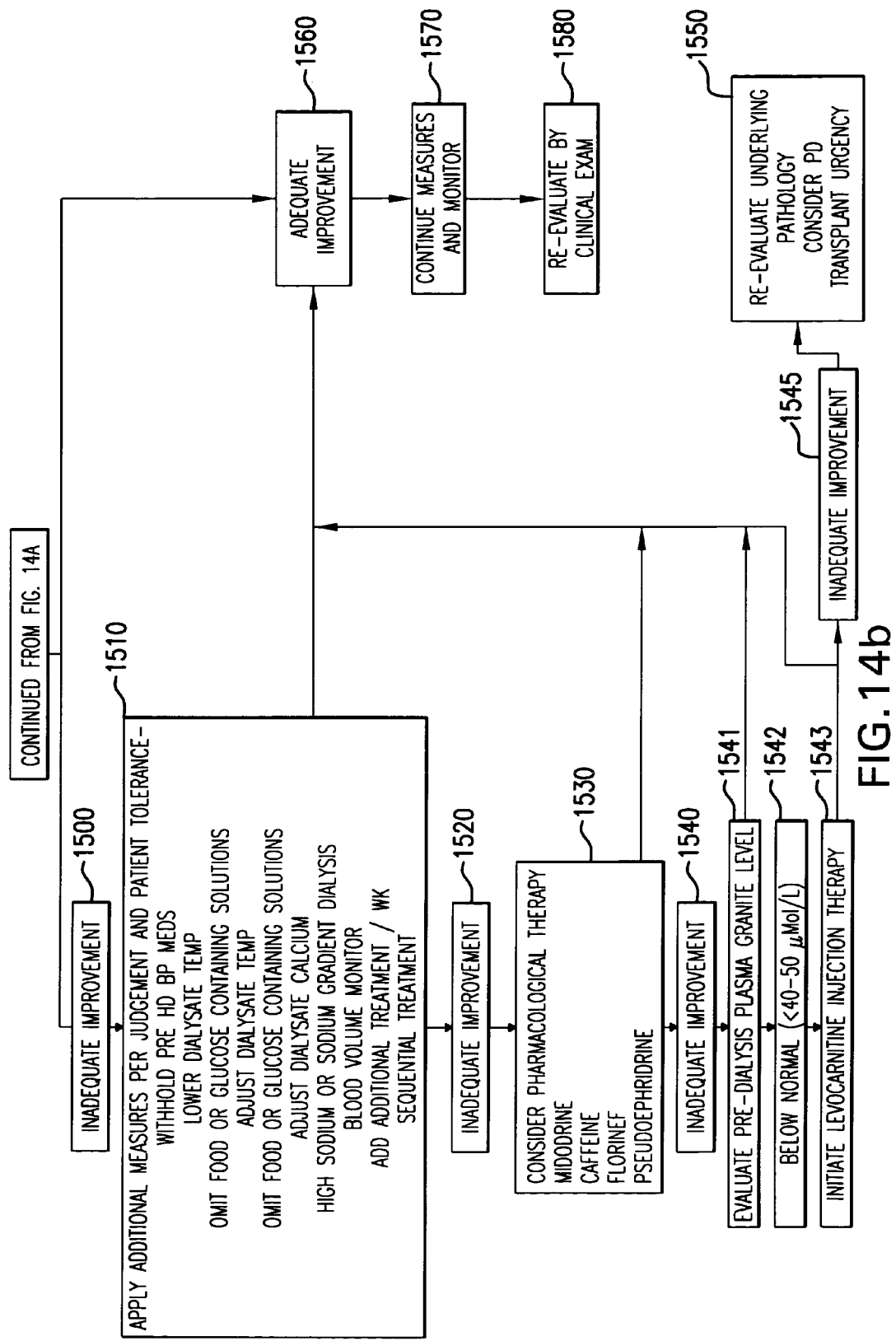
FIG. 14b is part two of the schematic diagram depicting the steps for a dialysis related hypotension diagnostic module.

Referring to FIG. 14b, if the initial measures of step 1490 show inadequate improvement 1500, the health care professional must apply additional measures 1510 according to his skill in the art and patient tolerance, such as withholding pre hemodialysis blood pressure medications, lowering dialysate temperature, omitting specific foods or glucose containing solutions, adjusting dialysate calcium, conducting high sodium or sodium gradient dialysis, using a blood volume monitor, adding additional treatment(s) per week, and conducting sequential treatments. If these measures provide adequate improvement 1560 for the patient's conditions, then the successful measures should be continued 1570 and the patient reevaluated as necessary 1580. If the additional measures of step 1510 show inadequate improvement 1520, then health care professional must consider pharmacological therapy measures 1530, such as Midodrine, Caffeine, Florinef (e.g., fludrocortisone acetetate), and Pseudoephridrine. If these pharmacological therapy measures provide adequate improvement 1560 for the patient's conditions, then the successful measures should be continued 1570 and the patient re-evaluated as necessary 1580. If the measures of step 1530 show inadequate improvement 1540, then the health care professional will evaluate the patient's pre-dialysis plasma carnitine concentration 1541, determine if the pre-dialysis camitine level is below normal 1542, and, if so, initiate levocamitine injection therapy 1543. If the levocamitine injection therapy 1543 provides adequate improvement 1560 for the patient's conditions, then the successful measures should be continued 1570 and the patient re-evaluated as necessary 1580. If the measures of step 1543 show inadequate improvement 1545, then the health care professional will reevaluate the underlying pathology, consider Parkinsons Disease, and evaluate transplant urgency. The steps of algorithm 1400 are charted in FIG. 15, such that a health care professional can effectively monitor the diagnostic process.

ESRD patients with the above conditions, as well as those with erythropoietin resistance, who are unresponsive to standard therapy are prescribed levocarnitine, generally 20 mg/kg/dialysis session. Once patients are on the therapy, the clinical outcome monitoring tool, as shown in FIG. 16, is used to evaluate a patient's response. The monitoring tool provides a map of key indicators from laboratory test results, patient intake of medication and supplements, and patient assessments. These key indicators are measured preferably before initiating levocarnitine injection therapy, after one month, after three months and after six months from the start of therapy.

As will be readily understood by one of ordinary skill in the art, the present invention can preferably be automated with software as is known in the art such that a computing device can be adapted to interact with health care professionals via a software interface and assist such professionals in appropriately utilizing and applying the algorithms and tools disclosed herein. In this manner, the health care professional can be automatically prompted to consider appropriate follow-up questions or considerations, or prompted to take appropriate diagnostic actions based upon the application of the algorithms and tools herein disclosed to the feedback data provided by the user. Once the health care professional has provided sufficient feedback data to the software automating the present invention, he or she can then be provided with a well-defined clinical picture that helps him or her identify a recommended course of action with respect to therapeutic carnitine administration.

Various modifications of the embodiments herein disclosed will be readily apparent to one skilled in the art after reading the above. For example, algorithms and tools automated by software according to alternative embodiments of the present invention may be adapted to store patient data and thereby automatically create patient logs and charts based upon the feedback data entered by the users of tools. Any and all such modifications are intended to be covered by the application as claimed.

What is claimed is:

1. A method for diagnosing clinical conditions related to carnitine deficiency common in a hemodialysis patient comprising the steps of:
    (a) obtaining symptom data from said hemodialysis patient;
    (b) applying at least one clinical diagnosis algorithm to said obtained symptom data from said hemodialysis patient;
    (c) identifying at least one symptom category based in part upon said step of applying at least one clinical diagnosis algorithm to said obtained symptom data from said hemodialysis patient; and
    (d) diagnosing at least one clinical condition related to carnitine deficiency common in said hemodialysis patient based at least in part on said step of identifying at least one symptom category;
    (e) recording diagnostic information concerning said at least one clinical condition in an electronic medium to create records for said hemodialysis patient;
    wherein said at least one symptom category includes at least one of selected from the group of secondary cardiomyopathy, dialysis related hypotension, cardiac arrhythmia, muscle wasting or weakness, muscle cramping, protein catabolism, lack of energy, and delayed or diminished response to erythropoietin; and
    wherein said at least one clinical algorithm is specific for at least one symptom category selected from the group of secondary cardiomyopathy, dialysis related hypotension, cardiac arrhythmia, muscle wasting or weakness, muscle cramping, protein catabolism, lack of energy, and delayed or diminished response to erythropoietin.

2. The method of claim 1, wherein said step of obtaining symptom data from said hemodialysis patient includes using at least one monitoring tool to obtain said symptom data from said hemodialysis patient.

3. The method of claim 2, wherein said at least one monitoring tool is communicatively coupled with a computer program and accessed via a computer that records said obtained symptom data from said hemodialysis patient.

4. The method of claim 1, wherein said steps of obtaining symptom data from said hemodialysis patient and diagnosing at least one clinical condition related to carnitine deficiency common in said hemodialysis patient comprise evaluating said hemodialysis patient's pre-dialysis plasma carnitine concentration, determining if said pre-dialysis carnitine level is below normal, and initiating at least one levocarnitine injection therapy if said pre-dialysis carnitine level is below normal.

5. The method of claim 4, wherein said steps of obtaining symptom data from said hemodialysis patient and diagnosing at least one clinical condition related to carnitine deficiency common in said hemodialysis patient comprise monitoring said levocarnitine injection therapy with at least one monitoring tool, wherein said monitoring tool provides a map of condition indicators selected from the group of laboratory test results, patient intake of medication and supplements, and patient assessments.

6. The method of claim 1 wherein said appropriate clinical algorithm for said symptom categories of secondary cardiomyopathy and hypotension during dialysis comprises the steps of:
    (a) evaluating said patient by a clinical exam, wherein said evaluating includes applying one or more initial treatments selected from the group consisting of controlling fluid volume during dialysis, controlling blood pressure, treating arrhythmia, adjusting hematocrit (HCT) hemoglobin (HGB), and reducing after-load;
    (b) if any of initial treatments provide adequate improvement upon evaluation, then continuing the improving treatment and monitoring the patient in subsequent clinical exams; and
    (c) if none of said types of treatments provide adequate improvement upon evaluation, then evaluating said patient's pre-dialysis plasma carnitine concentration, determining if the pre-dialysis carnitine level is below normal, and, if so, initialing levocarnitine injection therapy.

7. The method of claim 6 wherein the results of each step (a), (b), and (c) of claim 6 are recorded in a charting tool that contains the steps of the appropriate clinical algorithm for said symptom categories of secondary cardiomyopathy and hypotension during dialysis.

8. The method of claim 1, wherein said at least one symptom category is cardiac arrhythmia.

9. The method of claim 1 wherein said appropriate clinical algorithm for said symptom categories of muscle wasting or weakness and muscle cramping comprises the steps:
    (a) examining the muscle groups of a patient with said muscle wasting or weakness and muscle cramping symptoms to determine if the patient exhibits demonstrable muscle weakness;
    (b) if no demonstrable muscle weakness is identified, then evaluating said patient for malaise/fatigue by evaluating dialysis specific factors;
    (c) if demonstrable muscle weakness is identified, then examining for effects of an arthritic joint, an injured joint, or a sensory abnormality as the cause of the apparent muscle weakness;
    (d) if arthritic joints, injured joints, or sensory abnormalities are found, then providing treatment for said aribiritic joints, injured joints, or sensory abnormalities;
    (e) if no sensory abnormalities, arthritic joints, or injured joints are found, then evaluating the stretch reflexes of said patient;

(f) if the evaluation shows decreased proximal stretch reflexes or predominant proximal weakness, then evaluating said patient for muscle myopathy; and (g) if muscle myopathy is found, then evaluating said patient to identify one or more etiologies selected from the group consisting of underlying infectious processes, underlying inflammatory processes, underlying malignant processes, thyroid disorder, Cushing's disease, alcohol or drug usage, uncontrolled hyperparathyroidism, osteomalacia, aluminum toxicity, and carnitine deficiency.

10. The method of claim 8 wherein the results of each step (a) through (g) of claim 10 are recorded in a charting tool that contains the steps of the appropriate clinical algorithm for said symptom categories of muscle wasting or weakness and muscle cramping.

11. The method of claim 8 wherein said step of evaluating said patient for malaise/fatigue comprises the steps of:

(a) evaluating a patient by clinical exam to rule out a non-renal illness or condition as the cause or origin of the malaise/fatigue symptoms;

(b) evaluating factors specific to dialysis, said factors including inadequate dialysis and incompletely compensated anemia;

(c) if inadequate dialysis is a possible cause of the malaise or fatigue symptoms, adjusting the dialysis;

(d) if the adjusted dialysis relives the symptoms of malaise or fatigue, then continuing the successful measures and re-evaluating the patient's condition;

(e) if the adjusted dialysis does not relieve the malaise/fatigue symptoms or if both inadequate dialysis and incompletely compensated anemia are excluded as possible causes of the malaise/fatigue symptoms, then evaluating the patient's pre-dialysis plasma carnitine concentration, determining if the pre-dialysis carnitine level is below normal, and, if so, initiating levocarnitine injection therapy;

(f) if incompletely compensated anemia is a possible cause of the malaise or fatigue symptoms, then adjusting the erythropoietin dose accordingly;

(g) if the adjusted erythropoietin dose relives the malaise/fatigue symptoms, then continuing the successful erythropoietin dosage and reevaluating the patient as necessary;

(h) if the adjusted erythropoietin dose does not relive the malaise/fatigue symptoms, then evaluating the patient for delayed/diminished response to erythropoietin.

12. The method of claim 11 wherein the results of each step (a) through (b) of claim 11 are recorded in a charting tool that contains the steps of the appropriate clinical algorithm evaluating said patient for malaise/fatigue.

13. The method of claim 11 wherein said appropriate clinical algorithm for said symptom category delayed or diminished response to erythropoietin comprises the steps of:

(a) evaluating said patient for iron deficiency and, if present, treating said iron deficiency;

(b) evaluating said patient for possible acquired infection, inflammation, or malignancy and, if present, treating said infection, inflammation, or malignancy;

(c) evaluating said patient for occult blood loss and, if present, identifying the source of bleeding and treating with appropriate measures;

(d) evaluating said patient for an underlying hematologic disease, including one or more of thalassemia, refractory anemia, or other myelodysplastic disorders and, if present, treating said hematologic disease;

(e) evaluating said patient for hemolysis and, if present, treating the hemolysis;

(f) evaluating said patient for osteitis fibrosa cystica and, if present, treating said osteitis fibrosa cystica;

(g) evaluating said patient for aluminum intoxication and, if present, treating with chelation therapy;

(h) evaluating said patient for vitamin deficiencies and, if present, treating said vitamin deficiencies; and (i) if none of the previous indications are present, evaluating the patient's pro-dialysis plasma carnitine concentration, determining if the pre-dialysis carnitine level is below normal, and, if so, initiating levocarnitine injection therapy.

14. The method of claim 13 wherein the results of each step (a) through (i) of claim 14 are recorded in a charting tool that contains the steps of said appropriate clinical algorithm for said symptom category delayed or diminished response to erythropoietin.

15. The method of claim 9 wherein said step of evaluating said patient for muscle myopathy comprises the steps of:

(a) evaluating for possible acquired infection, inflammation, or malignancy and, if present, treating said acquired infection, inflammation, or malignancy;

(b) evaluating for possible thyroid disorders and, if present, treating said thyroid disorder;

(c) evaluating for Cushing's disease and, if present, treating said Cushing disease with drug therapy or surgery;

(d) evaluating for alcohol or drug use, and, if present, eliminating the alcohol or drug use;

(e) evaluating for uncontrolled hyperparathyroidism, and, if present, treating said hyperparathyroidism with suppressive therapy or surgery;

(f) evaluating for osteomalacia and, if present, treating said osteomalacia;

(g) evaluating for aluminum toxicity, if present, treating said aluminum toxicity;

(h) if none of the previous etiologies are present, evaluating the patient's pre-dialysis plasma carnitine concentration, determine if the pre-dialysis carnitine level is below normal, and, if so, initiating levocarnitine injection therapy.

16. The method of claim 15 wherein the results of each step (a) through (h) of claim 16 are recorded in a charting tool that contains the steps of the appropriate clinical algorithm evaluating said patient for muscle myopathy.

17. The method of claim 1, wherein said appropriate clinical algorithm for said symptom category dialysis related hypotension comprises the steps of:

(a) evaluating said patient by a clinical exam;

(b) determining whether symptoms of hypotension indicate an acute episode or a chronic sustained condition;

(c) if the symptoms indicate an acute episode, then initiating immediate corrective measures as described in steps (d) and (e) below;

(d) if the acute episode is not indicative of repetitive intradialytic hypotension, then continuing intermittent acute treatment;

(e) if the acute episode is indicative of repetitive intradialytic hypotension, then the applying one or more initial measures selected from the group of: using a machine with ultrafiltration control, counseling patient to limit salt, aiming for intradialytic weight gain greater than 1 kg/d, re-evaluating dry weight and avoiding ultrafiltration below the dry weight value, using bicarbonate containing dialysate, and reviewing anemia treatment to see if improvements are necessary;

(f) if the symptoms are a chronic sustained condition, then conducting one or more diagnostic selected from the group of: electrocardiograms, evaluating for pericarditis, testing for congestive heart failure (CHF), considering possible valve problems, checking for ischemia, testing for infections, considering hematologic disorders, and evaluating for sepsis;

(g) if any of said diagnostics indicates persistent hypotension despite treatment of the underlying condition, then applying said initial measures;

(h) if any of said diagnostics indicate hypotension is related to an underlying condition, then continuing treatment of the underlying condition, as necessary;

(i) if said initial measures do not provide a desired level of improvement, applying one or more additional measures selected from the group of: withholding pre hemodialysis blood pressure medications, lowering dialysate temperature, omitting specific foods or glucose containing solutions, adjusting dialysate calcium, conducting high sodium or sodium gradient dialysis, using a blood volume monitor, adding additional treatment(s) per week, and conducting sequential treatments;

(j) if said additional measures provide adequate improvement for the patient's conditions, then continuing the successful measures and reevaluating the patient as necessary;

(k) if said additional measures of step provide inadequate improvement, then considering one or more pharmacological therapy measures selected from the group of: midodrine, caffeine, fludrocortisone acetate, and pseudoephridrine;

(l) if said pharmacological therapy measures provide adequate improvement for said patient's conditions, then continuing the successful measures and reevaluating the patient as necessary; and (m) if said pharmacological therapy measures provide inadequate improvement, then evaluating the patient's pre-dialysis plasma carnitine concentration, determine if the pre-dialysis carnitine level is below normal, and, if so, initiating levocarnitine injection therapy.

18. The method of claim 17 wherein the results of each step (a) through (m) of claim 18 are recorded in a charting tool that contains the steps of the appropriate clinical algorithm evaluating said patient for dialysis related hypotension.

19. The method of claim 8, further comprising the steps of:

(a) evaluating said hemodialysis patient by a clinical exam;

(b) determining whether said symptom data from said hemodialysis patient is related to an underlying medical condition or to effects from a dialysis process;

(c) providing appropriate treatment relating to said underlying condition and monitoring said hemodialysis patient in at least one subsequent clinical exam, if said cardiac arrhythmia symptoms are related to an underlying medical condition;

(d) adjusting said dialysis process using at least one technique selected from the group of optimizing the volume status, adjusting the dialysate of said dialysis process, prolonging said dialysis process moderate fluid shifts, and administering oxygen during said dialysis process, if the arrhythmia symptoms are related to said dialysis process; and (e) initiating levocarnitine injection therapy if any of said adjustments to said dialysis process do not control the arrhythmia symptoms.

* * * * *